United States Patent
Gülec

[11] Patent Number: 5,349,103
[45] Date of Patent: Sep. 20, 1994

[54] PREPARATION OF AROMATIC NITRILES

[75] Inventor: Bilge Gülec, Basel, Switzerland

[73] Assignee: Ciba-Geigy Corporation, Ardsley, N.Y.

[21] Appl. No.: 184,617

[22] Filed: Jan. 21, 1994

[30] Foreign Application Priority Data

Jan. 28, 1993 [CH] Switzerland .................... 238/93

[51] Int. Cl.$^5$ ................................ C07C 253/00
[52] U.S. Cl. ........................................ 558/314
[58] Field of Search ............................ 558/314

[56] References Cited

U.S. PATENT DOCUMENTS

| | | | |
|---|---|---|---|
| 4,235,807 | 11/1980 | Fuhlhage | 260/465 G |
| 4,456,562 | 6/1984 | Tamura et al. | 558/314 |
| 4,808,746 | 2/1989 | Nishimura et al. | 558/314 |
| 5,281,744 | 1/1994 | Drent | 558/314 |

FOREIGN PATENT DOCUMENTS 0080700 4/1986 European Pat. Off. .
2198728 6/1988 United Kingdom .

OTHER PUBLICATIONS

Chemical Abstract 99:53294z (1983); Chiriac.
C.A. 85:93176e (1976); Liebecher.
C.A. 90:15177m (1979); Olah, et al.
C.A. 114:206700j (1991); Shi, et al.
Journal of Nanjing University, vol. 26(2) 1990, pp. 263–266.
Y. Chem. Soc. 1933 IX p. 43; Shoppee.

*Primary Examiner*—Joseph Paul Brust
*Attorney, Agent, or Firm*—Michele A. Kovaleski

[57] ABSTRACT

A process for the preparation of a nitrile of formula

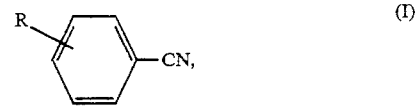

(I)

wherein R is hydrogen, $C_1$–$C_4$alkyl or phenyl, by reaction of an aldehyde of formula

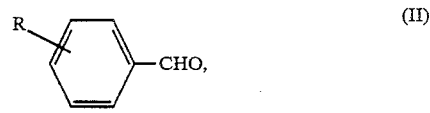

(II)

wherein R is as defined above, with hydroxylamine sulfate and subsequent dehydration, which process comprises carrying out the reaction in propionic acid in the presence of a salt of propionic acid by heating to an external temperature in the range from 140° to 165° C., preferably from 150° to 160° C., for 2 to 6 hours, preferably for 3 to 5 hours, under atmospheric pressure, and simultaneously distilling the mixture of propionic acid and water from the system until a solution forms, and thereafter removing the mixture of propionic acid and water at 100°–130° C., preferably 110°–120° C., by vacuum distillation, and then isolating the resultant nitrile by standard procedures.

7 Claims, No Drawings

PREPARATION OF AROMATIC NITRILES

The present invention relates to the preparation of aromatic nitriles by reacting corresponding aldehydes with hydroxylamine sulfate in propionic acid in the presence of a salt of propionic acid.

The reaction of aldehydes with hydroxylamine salts and subsequent dehydration of the resultant oxime to the nitrile has long been known. Different methods of dehydration have been proposed, inter alia in C.A. 85, 93176e (1976) by heating in dimethyl formamide, in EP-B 80700 by azeotropic distillation of the water of reaction from the system using a water-immiscible solvent that forms an azeotropic mixture, in Synthesis 1979, 2, 112–113 and in Huaxue Shiji 1990, 12(5), 314, 292 by heating in formic acid, in Journal of Nanjing Univ. 1990, 26(2), 263–266, by heating in formic acid or glacial acetic acid and in J. Chem. Soc. 1933, IX, 43, by heating in acetic anhydride. For toxicological and environmental reasons, the use of dimethyl formamide or of water-immiscible solvents on an industrial scale is to be as far as possible avoided. Although very good results are obtained using formic acid, the strongly corrosive action, toxicity and troublesome regeneration of this acid makes its use inadvisable. Some of these shortcomings could have been eliminated by using acetic acid, but it has been found that certain benzonitriles can be obtained therewith in only very poor yield.

Very surprisingly, it has now been found that the use of a weaker acid such as propionic acid makes it possible to obtain the same nitriles in substantially better and entirely satisfactory yield. This is all the more surprising in the light of the teaching of U.S. Pat. No. 4,235,407, according to which the reaction of a benzaldehyde with hydroxylamine to the benzonitrile using an organic acid (also including propionic acid) as solvent takes place only in the presence of a dehydrating agent such as acetic or propionic anhydride, phosphorus pentoxide or dimethyl acetal. The drawbacks referred to above can thereby be substantially avoided, for propionic acid is toxicologically harmless, far less corrosive and can be easily regenerated.

Accordingly, the invention relates to a process for the preparation of a nitrile of formula

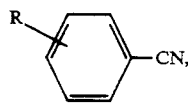
(I)

wherein R is hydrogen, $C_1$–$C_4$alkyl or phenyl, by reaction of an aldehyde of formula

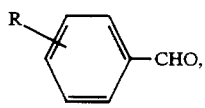
(II)

wherein R is as defined above, with hydroxylamine sulfate and subsequent dehydration, which process comprises carrying out the reaction in propionic acid in the presence of a salt of propionic acid by heating to an external temperature in the range from 140° to 165° C., preferably from 150° to 160° C., for 2 to 6 hours, preferably for 3 to 5 hours, under atmospheric pressure, and simultaneously distilling the mixture of propionic acid and water from the system until a solution forms, and thereafter removing the mixture of propionic acid and water at 100°–130° C., preferably 110°–120° C., by vacuum distillation, and then isolating the resultant nitrile by standard procedures.

The reaction is carried out in accordance with the following reaction scheme:

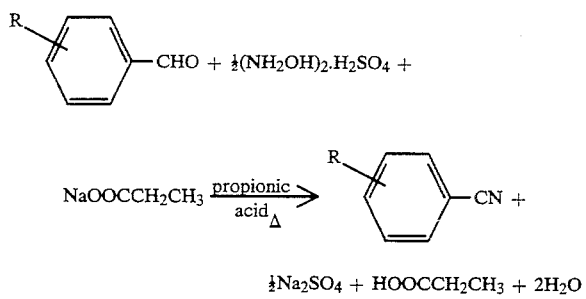

R defined as $C_1$–$C_4$alkyl is methyl, ethyl, n-propyl, isopropyl, n-butyl, sec-butyl or tert-butyl.

An alkali metal salt, preferably sodium propionate, may suitably be used as a salt of propionic acid.

R is preferably in 4-position and is preferably tert-butyl or, most preferably, phenyl.

The aldehydes of formula II are known compounds.

The propionic acid is conveniently used in an amount of 10 to 20 mol, preferably 15 to 18 mol, based on 1 mol of aldehyde.

Hydroxylamine sulfate is used in approximately stoichiometric proportion, preferably in slight excess, i.e. 0.505 to 0.58 mol, based on 1 mol of aldehyde.

Sodium propionate is suitably used in an amount of 1.05 to 1.3 mol, based on 1 mol of hydroxylamine sulfate.

The nitriles obtained by the process of this invention am useful intermediates for, inter alia, the synthesis of diketopyrrolopyrrole pigments. p The following Examples illustrate the invention.

EXAMPLE 1

606.0 g (8.2 mol) of propionic acid are charged to a sulfonating flask at room temperature and 91.10 g (0.5 mol) of 4-biphenylaldehyde, 28.82 g (0.3 mol) of sodium propionate and 45.14 g (0.28 mol) of hydroxylamine sulfate are added. This mixture is heated for 30 minutes to an external temperature of 153° C. and afterwards stirred for 3 hours at this temperature under normal pressure. During this time, a solvent mixture consisting of propionic acid and water is continuously distilled from the system. After distillation for 3 hours a solution forms.

The external temperature is lowered to 120° C., a vacuum is applied, and a solvent mixture consisting of propionic acid and water is continuously distilled from the system over 2 hours at this temperature under a vacuum of c. 390 mbar.

The vacuum is then released, and the residue is cooled to approximately room temperature and precipitated by pouring it into a mixture of ice/water. The precipitate is isolated by filtration and washed with water until neutral. The yield of crude product is 89.3 g. The 4-biphenylnitrile is obtained in 85.7% purity (c. 85% of theory).

EXAMPLE 2

606.0 g (8.2 mol) of propionic acid are charged to a sulfonating flask at room temperature and 81.15 g (0.5 mol) of 4-tert-butylbenzaldehyde, 28.82 g (0.3 mol) of sodium propionate and 45.14 g (0.28 mol) of hydroxylamine sulfate are added. This mixture is heated for 30 minutes to an external temperature of 158° C. and afterwards stirred for 5 hours at this temperature under normal pressure. During this time, a solvent mixture consisting of propionic acid and water is continuously distilled from the system. After distillation for 5 hours a solution forms.

The external temperature is then lowered to 120° C., a vacuum is applied, and a solvent mixture consisting of propionic acid and water is continuously distilled from the system over 2 hours at this temperature under a vacuum of c. 390 mbar.

The vacuum is then released, the external temperature is lowered to 100° C., 28.82 g of sodium propionate are again added, and the reaction mixture is stirred under normal pressure for 15 minutes.

After stirring has been discontinued, a vacuum of c. 50–65 mbar is applied, the external temperature is raised to 120° C., and the remaining propionic acid is distilled from the system.

The oily residue is washed until neutral at room temperature with sodium hydrogencarbonate and water and the organic phase is then separated. The yield of crude product is 83.9 g and 4-tert-butylbenzonitrile is obtained in 71.1% purity (c. 74% of theory).

EXAMPLE 3

370.4 g (5 mol) of propionic acid are charged to a 1 liter sulfonating flask at room temperature and 58.58 g (0.5 mol) of 4-methylbenzaldehyde, 14.55 g (0.15 mol) of sodium propionate and 45.14 g (0.28 mol) of hydroxylamine sulfate are added. This mixture is heated for 30 minutes to an external temperature of 153° C. and afterwards stirred for c. 10 minutes at this temperature under normal pressure. After stirring for 10 minutes a solution forms.

The external temperature is then lowered to 120° C., a vacuum is applied, and a solvent mixture consisting of propionic acid and water is distilled from the system over 4 hours at this temperature under a vacuum of c. 400 mbar.

The vacuum is then released, the external temperature is lowered to 100° C., 48.7 g (0.51 mol) of sodium propionate are added and the reaction mixture is stirred under normal pressure for 15 minutes.

After stirring has been discontinued, the reaction mixture is cooled to room temperature and filtered over a glass fit. The yield of 4-methylbenzonitrile is 46.07 g (78.65% of theory).

EXAMPLE 4

606.0 g (8.2 mol) of propionic acid are charged to a 1 liter sulfonating flask at room temperature and 53.06 g (0.5 mol) of benzaldehyde, 14.55 g (0.15 mol) of sodium propionate and 45.14 g (0.28 mol) of hydroxylamine sulfate are added. This mixture is heated for 30 minutes to an external temperature of 153° C. and afterwards stirred for c. 20 minutes at this temperature under normal pressure. After stirring for 20 minutes a solution forms.

The external temperature is then lowered to 120° C., a vacuum is applied, and a solvent mixture consisting of propionic acid and water is continuously distilled from the system over 4 hours at this temperature under a vacuum of c. 400 mbar.

The vacuum is then released, the external temperature is lowered to 100° C., 48.7 g (0.51 mol) of sodium propionate are added and the reaction mixture is stirred under normal pressure for 15 minutes.

After stirring has been discontinued, the reaction mixture is cooled to room temperature and filtered over a glass fit. The yield of benzonitrile is 42.11 g (81.7% of theory).

What is claimed is:

1. A process for the preparation of a nitrile of formula

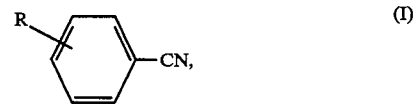

wherein R is hydrogen, $C_1$–$C_4$alkyl or phenyl, by reaction of an aldehyde of formula

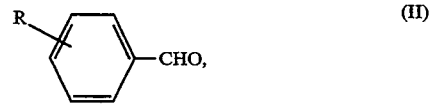

wherein R is as defined above, with hydroxylamine sulfate and subsequent dehydration, which process comprises carrying out the reaction in propionic acid in the presence of a salt of propionic acid by heating to an external temperature in the range from 140° to 165° C. for 2 to 6 hours, under atmospheric pressure and simultaneously distilling the mixture of propionic acid and water from the system until a solution forms, and thereafter removing the mixture of propionic acid and water at 100°–130° C. by vacuum distillation, and then isolating the resultant nitrile by standard procedures.

2. A process according to claim 1, wherein R is in 4-position.

3. A process according to claim 2, wherein R is tert-butyl or phenyl.

4. A process according to claim 2, wherein R is phenyl.

5. A process according to claim 1, wherein the propionic acid is added in an amount of 10 to 20 mol, based on 1 mol of aldehyde.

6. A process according to claim 5, wherein the hydroxylamine sulfate is added in an amount of 0.505 to 0.55 mol based on 1 mol of aldehyde, and the sodium propionate is added in an amount of 1.05 to 1.3 mol, based on 1 mol of hydroxylamine sulfate.

7. A process according to claim 1, wherein the reaction is carried out by heating to an external temperature in the range from 150° to 160° C. for 3 to 5 hours and the mixture of propionic acid and water is removed by vacuum distillation at 110°–120° C.

* * * * *